(12) United States Patent
Walish et al.

(10) Patent No.: US 9,931,129 B2
(45) Date of Patent: Apr. 3, 2018

(54) SMALL FRAGMENT RETRIEVAL DEVICE

(71) Applicant: Gyrus ACMI, Inc., Southborough, MA (US)

(72) Inventors: Judy L. Walish, West Roxbury, MA (US); Lawrence J. St. George, Sudbury, MA (US); Antonio E. Prats, Shrewsbury, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 252 days.

(21) Appl. No.: 14/662,992

(22) Filed: Mar. 19, 2015

(65) Prior Publication Data
US 2016/0270805 A1  Sep. 22, 2016

(51) Int. Cl.
*A61B 17/22* (2006.01)
*A61B 17/221* (2006.01)
*A61B 17/00* (2006.01)

(52) U.S. Cl.
CPC ............ *A61B 17/221* (2013.01); *A61B 17/22* (2013.01); *A61B 17/22031* (2013.01); *A61B 2017/00858* (2013.01); *A61B 2017/00876* (2013.01); *A61B 2017/00951* (2013.01); *A61B 2017/00955* (2013.01); *A61B 2017/2215* (2013.01); *A61B 2017/22035* (2013.01)

(58) Field of Classification Search
CPC ........ A61B 17/22031; A61B 17/22032; A61B 2017/22034; A61B 2017/22035; A61B 17/221; A61B 2017/2212; A61B 2017/2215; A61B 2017/2217; A61B 2017/246; A61F 2/0018; A61F 11/006; A61F 13/38; A61F 13/36
See application file for complete search history.

(56) References Cited

U.S. PATENT DOCUMENTS

| | | | | |
|---|---|---|---|---|
| 3,792,699 A * | 2/1974 | Tobin | ................. | A61B 10/0096 401/133 |
| 3,935,863 A * | 2/1976 | Kliger | ..................... | A61F 13/38 604/267 |
| 3,958,571 A * | 5/1976 | Bennington | ........ | A61M 35/006 401/196 |
| 4,465,078 A * | 8/1984 | Manning | ................. | A61F 13/38 600/572 |

(Continued)

FOREIGN PATENT DOCUMENTS

DE  102010014778 A1  10/2011
EP      2355717 B1   2/2014

(Continued)

OTHER PUBLICATIONS

J.H. Jung and Y.P. Lee, Magnetic Characterization of Bio-Magnetic Nanoparticles: ferritin, Journal of the Korean Physical Society, Apr. 2011, pp. 966-968.

(Continued)

*Primary Examiner* — Jonathan Miles
(74) *Attorney, Agent, or Firm* — Harrington & Smith

(57) ABSTRACT

A medical device for retrieving small fragments from within a patient's anatomy includes a collection wire configured for entering the patient's anatomy. The collection wire includes a distal end with a plurality of tips that are configured to attract stone fragments from the patient's anatomy.

15 Claims, 3 Drawing Sheets

(56) References Cited

U.S. PATENT DOCUMENTS

| | | | |
|---|---|---|---|
| 4,718,889 A * | 1/1988 | Blasius, Jr. | A61F 13/38 604/1 |
| 4,953,560 A * | 9/1990 | Samuels | A61B 10/00 435/289.1 |
| 5,158,532 A * | 10/1992 | Peng | A45D 40/28 15/144.1 |
| 5,531,671 A * | 7/1996 | Bennett | A61F 13/385 15/118 |
| 5,707,236 A * | 1/1998 | Swanson | A61C 19/001 433/219 |
| 6,096,053 A | 8/2000 | Bates | |
| 7,563,239 B1 * | 7/2009 | Hudson | A61F 13/38 15/244.1 |
| 7,883,516 B2 | 2/2011 | Huang et al. | |
| 8,753,351 B2 | 6/2014 | Huang et al. | |
| 2001/0022063 A1 * | 9/2001 | Korteweg | A61F 13/38 53/428 |
| 2002/0133110 A1 * | 9/2002 | Citow | A61F 5/0093 604/1 |
| 2005/0137515 A1 * | 6/2005 | King | A61F 13/38 604/1 |
| 2006/0085018 A1 * | 4/2006 | Clevenger | A61F 11/006 606/162 |
| 2007/0004995 A1 * | 1/2007 | Horn | A61F 13/38 604/2 |
| 2007/0225729 A1 * | 9/2007 | Cheng | A61B 17/221 606/127 |
| 2007/0255175 A1 * | 11/2007 | Sangha | A61B 10/0045 600/572 |
| 2007/0299457 A1 * | 12/2007 | Morales | A61F 11/006 606/162 |
| 2008/0045881 A1 | 2/2008 | Teitelbaum et al. | |
| 2008/0208100 A1 * | 8/2008 | Wolff | A61F 13/38 604/1 |
| 2009/0112241 A1 * | 4/2009 | Bar | A61F 11/006 606/162 |
| 2009/0136594 A1 | 5/2009 | McLeroy et al. | |
| 2009/0192485 A1 | 7/2009 | Heuser | |
| 2011/0106121 A1 * | 5/2011 | Zaldivar | A61F 13/36 606/162 |
| 2011/0152920 A1 | 6/2011 | Eckhouse et al. | |
| 2011/0270290 A1 * | 11/2011 | Nadam | A61F 13/38 606/162 |
| 2013/0345703 A1 | 12/2013 | Phelps et al. | |
| 2014/0024887 A1 | 1/2014 | Ishii et al. | |
| 2014/0276407 A1 | 9/2014 | DeVries et al. | |
| 2014/0302051 A1 | 10/2014 | Askari et al. | |
| 2015/0351968 A1 * | 12/2015 | Shane | A61F 11/006 606/162 |

FOREIGN PATENT DOCUMENTS

| | | |
|---|---|---|
| JP | 2006314811 A | 11/2006 |
| WO | 20150006782 A1 | 1/2015 |

OTHER PUBLICATIONS

S.P.Sase, J.V.Ganu and N. Nagane, Osteopontin: A Novel Protein Molecule, Indian Medical Gazette, Feb. 2012, p. 62.

C. Albornoz and S.E. Jacobo, Preparation of a biocompatible magnetic film from an aqueous ferrofluid, Journal of Magnetism and Magnetism Materials 305 (2006) 12-15.

C. Zhong, T. Gurry, A.A. Cheng, J. Downey, Z. Deng, C.M. Stultz and T.K. Lu, Strong underwater adhesives made by self-assembling multi-protein nanofibres, Nature Nanotechnology, vol. 9, Oct. 2014, pp. 858-866.

K. Bullis, Climbing Walls with Carbon Nanotubes, A new kind of tape mimics the qualities of gecko feet, MIT Technology Review, v1.13.05.10.

P. Patel, Nanoglue Sticks Underwater,Geckos and mussels inspire a better glue, MIT Technology Review, v1.13.05.10.

Saeed R. Khan Editor, Calcium Oxalate in Biological Systems,CRC Press, Inc Boca Raton FL, copyright 1995.

* cited by examiner

SMALL FRAGMENT RETRIEVAL DEVICE

FIELD

The present disclosure relates to a medical device. More specifically, the present disclosure relates to a device for retrieving small fragments.

BACKGROUND

The statements in this section merely provide background information related to the present disclosure and may or may not constitute prior art.

Lithotripsy is a common method for fragmenting stones, or calculi, in the urinary tract, kidneys, and/or bladder. Lithotripsy, however, can leave stone fragments, which act as nucleation sites for future stone formation, for example, in the lower pole of a kidney. These fragments remain in the patient after the procedure mostly because of the difficulty in capturing very small fragments of dust employing conventional removal devices such as, for example, stone baskets.

Typical corrective actions may include one or more of the following: monitoring for future stone formation, performing additional ureteroscopic procedures, or percutaneous nephrolithotomy. Among the literature that can pertain to this technology include the following patent documents and published patent applications: EP 2355717, US 20090136594, JP 2006314811, U.S. Pat. Nos. 7,883,516, and 8,753,351, the entire contents of which are incorporated herein by reference for all purposes.

Accordingly, there is a need for a device that can be employed with lithotripsy that removes small fragments. It would be desirable to have mechanisms which attract, retain, and contain stone fragments to reliably remove small stone fragments and debris.

SUMMARY

The present disclosure provides an improved small fragment retrieval device and a method of using the small fragment retrieval device.

In one aspect, the present disclosure provides a medical device for retrieving small fragments from within a patient's anatomy. The medical device includes a collection wire configured for entering a patient's anatomy. The collection wire includes a distal end with a plurality of tips that are configured to attract stone fragments from the patient's anatomy.

The medical device may be further characterized by one or any combination of the features described herein, such as, for example: the plurality of tips are a plurality of curled tips; the tips of the plurality of tips extend laterally from the distal end, the tips of the plurality of tips being spaced apart and positioned about the distal end in a spiral arrangement; the tips of the plurality of tips are a plurality of filaments; the filaments of the plurality of filaments are intertwined into a fibrous structure; the medical device further comprises a wire mesh that selectively surrounds the plurality of tips; the wire mesh selectively surrounds the plurality of tips by moving distally and proximally relative to the plurality of tips; the wire mesh is configured to collapse over the plurality of tips; the collection wire is formed of molded silicone; the collection wire is formed of molded plastic; the plurality of tips include a magnetic outer surface; the plurality of tips include a calcium attractive outer surface.

In another aspect, the present disclosure provides a method of collecting stone fragments from a patient's anatomy including one or more of the following steps: inserting a collection wire into the patient's anatomy; positioning a distal end of the collection wire near an anatomical region containing stone fragments, the distal end having a plurality of tips; and attracting the stone fragments to the collection wire with the plurality of tips. The method may be further characterized by one or any combination of the features described herein, such as, for example: the method further comprises surrounding the stone fragments and the plurality of tips with a wire mesh; and the plurality of tips include an attractive outer surface that attracts the stone fragments.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses.

Figure 1A:
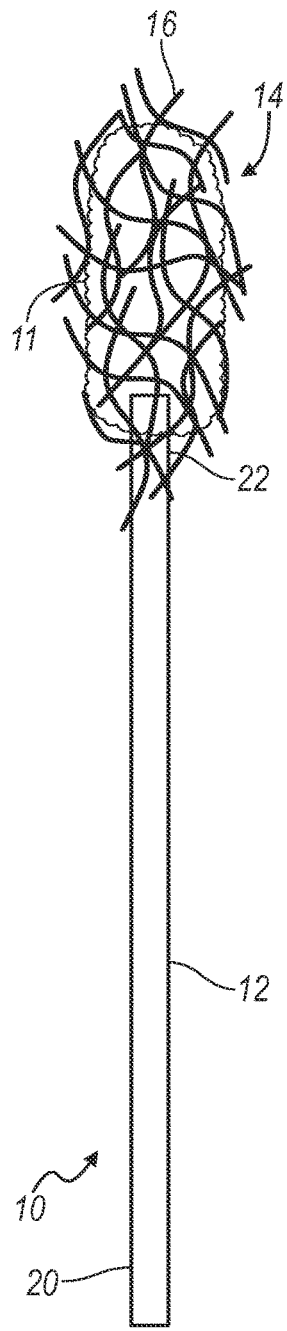
FIG. 1A is a side view of a small fragment retrieval device in accordance with the principles of the present invention.

Referring now to the drawings, a small fragment retrieval device or collection wire embodying the principles of the present invention is illustrated in FIG. 1A and designated at 10. The collection wire 10 includes a shaft 12 with a proximal end 20 and a distal end 22. A plurality of tips 16 is attached to the distal end 22 of the shaft 12. In the configuration shown in FIG. 1A, the plurality of tips 16 is a plurality of filaments that are intertwined into a fibrous structure 14. The fibrous structure 14 is porous to allow fluid to flow through it while capturing small stone fragments and dust particles that are generated during lithotripsy.

When in use, a physician inserts the collection wire 10 into a patient's anatomy so that the fibrous structure 14 is positioned near an anatomical region of the patient that contains small stone fragments and dust which may have been produced, for example, by lithotripsy. As the physician sweeps the fibrous structure 14 around the anatomical region, the small stone fragments and dust are collected by the filaments 16. After the stone fragments and dust have been accumulated into a conglomeration of stone fragments 11, the physician pulls on the shaft 12 to retrieve the collection wire 10 along with the conglomeration of stone fragments 11 from the patient's anatomy.

It is contemplated that the fibrous structure may include synthetic balls of material comprising rayon or polyester, ultra-high-molecular-weight polyethylene (UHMWPE), other polymers, or the like. It is further contemplated that individual filaments of the fibrous structure may be coated with a flexible polymer or adhesive, such as for example amyloid fiber, natural amyloid fiber, mussel foot proteins (Mfps), or bundles of carbon nanotubes to make use of microscale van der Waals forces to capture the small stone fragments or dust (that is, "gecko tape").

Figure 1B:
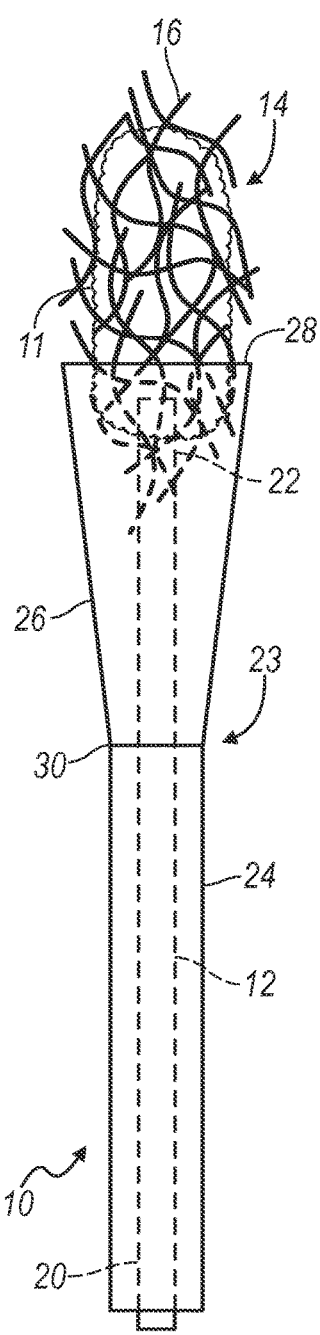
FIG. 1B is a side view of the small fragment retrieval device shown in FIG. 1A in an alternative configuration.

Referring further to FIG. 1B, the collection wire 10 may include an optional containment device 23. The containment device 23 includes a sheath 24 and an expandable cone-shaped basket 26 attached to a distal end 30 of the sheath 24. The cone-shape basket 26 may be made from a solid material or from a mesh.

When in use, the sheath 24 and the basket 26 are initially placed over the shaft 12 of the collection wire 10 such that basket 26 is collapsed about the shaft 12. After the conglomeration of stone fragments 11 is collected by the filaments 16 as described above, the physician pulls the proximal end 20 of the shaft 12 relative to the containment device 23. As this occurs, the basket expands or opens as the conglomeration of stone fragments 11 is pulled into the basket 26. The physician then removes the collection wire 10 along with the conglomeration of stone fragments 11 contained in the basket 26 from the patient's anatomy.

Figure 2:
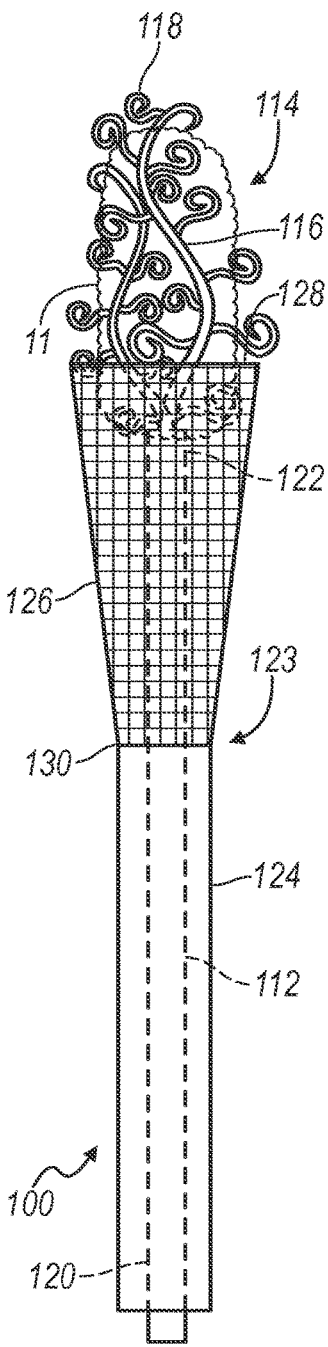
FIG. 2 is a side view of another small fragment retrieval device in accordance with the principles of the present invention.

Turning now to FIG. 2, there is shown an alternative small fragment retrieval device or collection wire 100 that includes a shaft 112 with a proximal end 120 and a distal end 122. A plurality of tips 114 is attached to the distal end 122 of the shaft 112. The plurality of tips 114 includes a plurality of primary curled tips 116 and a plurality of secondary curled tips 118 attached to the primary curled tips 116. The collection wire 100 may include a containment device 123 that includes a sheath 124 and an expandable basket 126 attached to a distal end 130 of the sheath 124. The basket 126 may be formed from a solid material or may have a mesh structure.

When in use, the sheath 124 and the basket 126 are initially placed over the shaft 112 such that the basket 126 is collapsed about the shaft 112. The collection wire 100 is inserted into a patient's anatomy so that the plurality of tips 114 is positioned near an anatomical region of the patient that contains small stone fragments and dust. As a physician sweeps the plurality of tips 114 around the anatomical region, the small stone fragments and dust are collected by the primary and secondary curled tips 116 and 118. After the stone fragments and dust have been accumulated into the conglomeration of stone fragments 11, the physician pulls on the proximal end 120 of the shaft 112 so that the conglomeration of stone fragments is pulled into the basket 126 as the basket 126 expands to an open state. The physician then retrieves the collection wire 100 along with the conglomeration of stone fragments 11 contained in the basket 126 from the patient's anatomy. In certain procedures, the collection wire 100 can be employed without the use of the containment device 123.

The plurality of tips 14 and 114 described above are generally flexible and are made of any suitable material such as, for example, plastic, silicone or metal. The filaments 16 of the collection wire 10 and the primary and secondary curled tips 116 and 118 of the collection wire 100 can be coated with an adhesive material. For example, the adhesive may be a calcium attractant adhesive. It is contemplated that the filaments, collection wire, and/or curled tips may be coated (for example, sinter bonded) with calcium oxalate or an alternative calcium-based mineral. Subsequently, a nanofunctional molecule, which may be a protein or a polyanionic macromolecule and which may be provided with a calcium attractive surface at both ends, is applied to the filaments, collection wire, and/or curled tips so as to attract stone dust or stone debris containing calcium oxalate. The nanofunctional molecule could be carboxylic acid-rich proteins, osteopontin, or prothrombin fragment 1, for example, or the like, and may be crosslinked with a second nanofunctional molecule. In this way, the nanofunctional molecule may be calcium attractive at two opposing ends and thereby attract and retain stone dust and debris to the filaments, curled tips, and/or collection wire. It is further contemplated that the nanofunctional molecule may be long enough such that multiple calcium attractive sites are provided on a single molecule. In this case, the nanofunctional molecule would be sufficient to attract and retain stone dust and debris to the filaments, curled tips, and/or collection wire.

Alternatively, the filaments 16 and the primary and secondary curled tips 116 and 118 may be coated with magnetic material to act as a magnetic attractant. It is contemplated that contacting kidney stones with ferrous or magnetic particles that are able to bind the kidney stone debris, and reacting the kidney stone debris with the ferrous or magnetic particles may cause the kidney stone debris to become attractable magnetically. In one aspect, the ferrous or magnetic particles may further comprise an agent that specifically binds the surface of the kidney stone debris selected from proteins that interact with calcium-based biominerals, such as carboxylic acid-rich proteins, osteopontin, prothrombin fragment 1. It is contemplated that the magnetic protein ferritin may be used as a second protein and crosslinked to one of the nanofunctional proteins, or first proteins, mentioned above and used for this purpose.

Figures 3A, 3B:
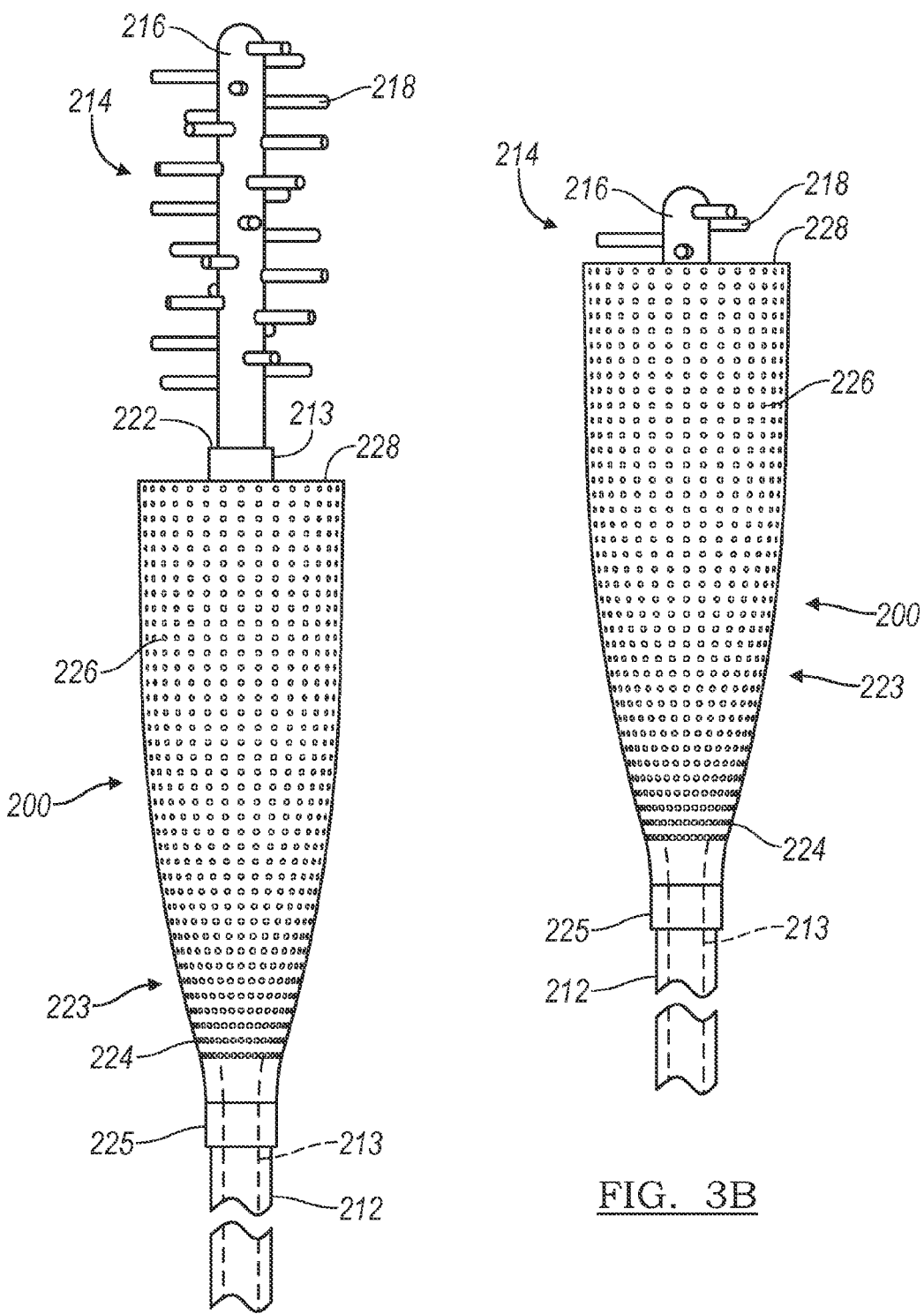
FIGS. 3A and 3B are side views of yet another small fragment retrieval device in accordance with the principles of the present invention.

Referring now to FIGS. 3A and 3B, there is shown yet another small fragment retrieval device or collection wire 200. The collection wire 200 includes a shaft 213 and a plurality of tips 214. The plurality of tips 214 may be formed integrally with a distal portion of the shaft 213, or the plurality of tips 214 may include a primary projection 216 attached the distal end 222 of the shaft 213. The plurality of tips 214 further includes a collection of projections 218 that extend substantially laterally from the distal portion of the shaft 213 or from the primary projection 216. As illustrated in FIG. 3A, the projections 218 are spaced apart and are arranged in a spiral pattern or arrangement about the primary projection 216. The plurality of tips can be coated with an adhesive, such as, for example, calcium attractant adhesive or a magnetic attractant.

The collection wire 200 also includes a containment device 223. The containment device 223 includes a sheath 212 and a basket 224 attached to a distal end 225 of the sheath 212. The basket 224 may be made of a solid material or a mesh-like structure with a plurality of holes 226.

When in use, the sheath 212 and the basket 224 are placed over the shaft 213. A physician inserts the retrieval device 200 into a patient's anatomy so that the plurality of tips 214 is positioned near an anatomical region of the patient that contains small stone fragments and dust. As the physician sweeps the plurality of tips 214 around the anatomical region, the small stone fragments and dust are collected by the collection of projections 218. After the stone fragments have been accumulated into a conglomeration of stone fragments, the physician pulls on the proximal end of the shaft 212 so that the conglomeration of stone fragments and dust are pulled into a distal end 228 of the basket 226. The physician then retrieves the collection wire 200 along with the conglomeration of stone fragments and dust contained in the basket 224 from the patient's anatomy. In certain procedures, the collection wire 200 can be employed without the use of the containment device 223.

It is contemplated that various substances and methods may be used to produce a flocculation or aggregation of stone dust or debris particulates prior to the various collection methods described herein being commenced. For example, flocculation may be accomplished through the creation of a low pH environment in the kidney. It is further contemplated that adding, ejecting, and/or inserting an adhesive agent such as polyethylenimine, biocompatible nanoadhesive such as alginate gel, cellulose gel, protein based gel, collagen, polysaccharide, chitosan gel, in vivo gel formulations which at least in part polymerize and/or gel at the target site in a human body to form a biocompatible hydrogel polymer, ferrogels, and/or biocompatible magnetic gels which may include polyvinyl alcohol and gluteraldehyde may help to aggregate stone dust or stone debris. It is contemplated that such an adhesive agent may be added, injected, and/or inserted with an additional device such as a catheter or out of an opening in a distal most end of the primary projection 216, for example. The adhesive agent may be given some time to collect stone dust or stone debris, the primary projection 216 or other collection device may be inserted into the region containing the adhesive agent to attract the adhesive agent containing stone dust and stone debris, the containment device 223 may surround the primary projection 216 or other collection device, and the device may be subsequently removed from a patient.

Figure 4:
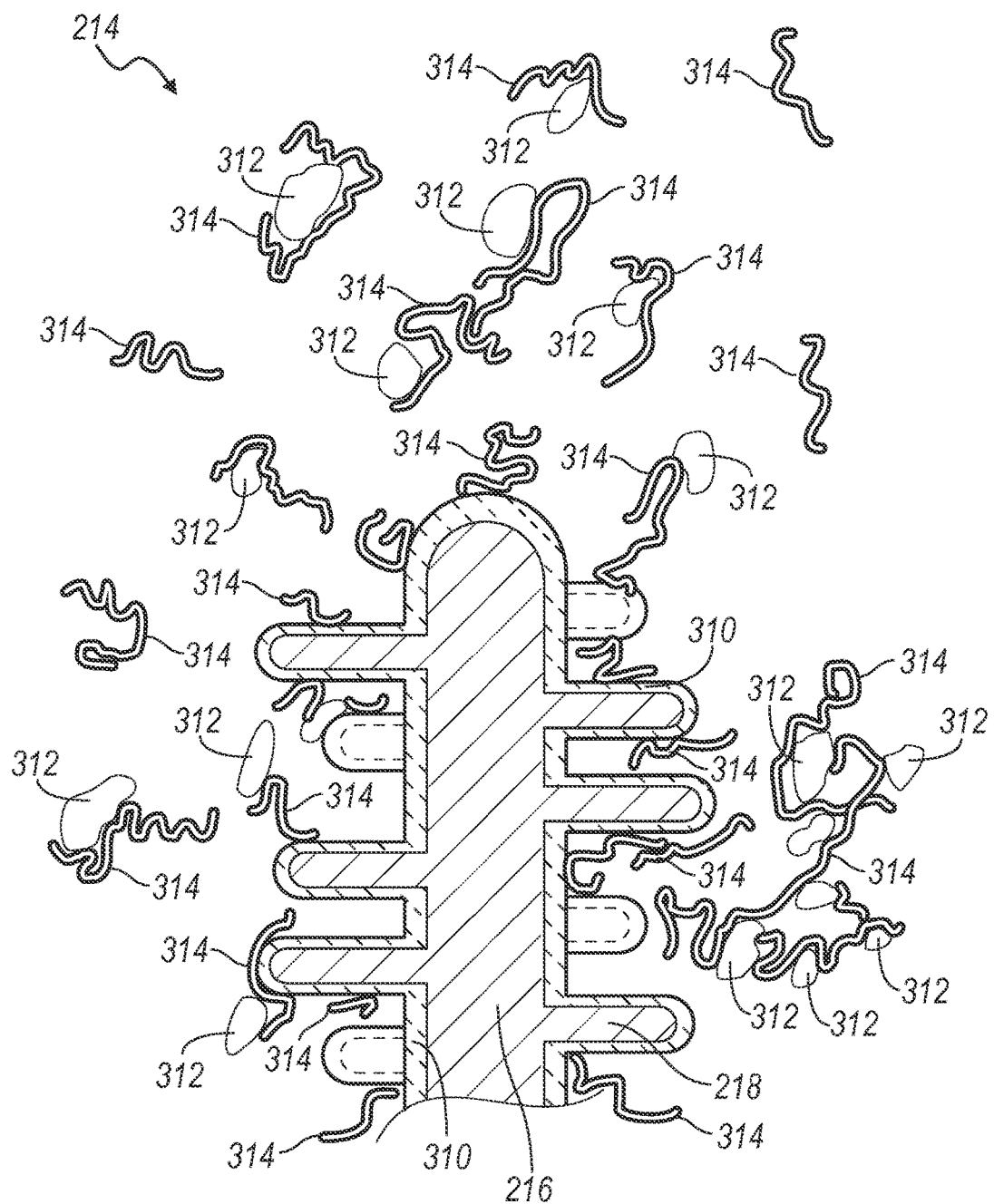
FIG. 4 is a side view of a portion of the retrieval device shown in FIGS. 3A and 3B coated with an attractant in accordance with the principles of the present invention.

In some arrangements, the plurality of tips 214, such as, for example, the primary projection 216 and the collection of projections 218, may be coated with a calcium attractant adhesive, similar to the coating described previously with respect to filaments 16 of the collection wire 10 and the primary and secondary curled tips 116 and 118 of the collection wire 100. For example, the plurality of tips 214 may be coated (for example, sinter bonded) with calcium oxalate or an alternative calcium-based mineral 310, as shown in FIG. 4. Subsequently, a nanofunctional molecule 314, which may be a protein or a polyanionic macromolecule and which may be provided with a calcium attractive surface at both ends, is applied to the plurality of tips 214 so as to attract stone dust or stone debris 312 containing calcium oxalate. The nanofunctional molecule 314 could be carboxylic acid-rich proteins, osteopontin, or prothrombin fragment 1, for example, or the like, and may be crosslinked with a second nanofunctional molecule. In this way, the nanofunctional molecule 314 may be calcium attractive at two opposing ends and thereby attract and retain stone dust and debris to the plurality of tips 214. It is further contemplated that the nanofunctional molecule 314 may be long enough such that multiple calcium attractive sites are provided on a single molecule. In this case, the nanofunctional molecule would be sufficient to attract and retain stone dust and debris 312 to the plurality of tips 214.

The description of the invention is merely exemplary in nature and variations that do not depart from the gist of the invention are intended to be within the scope of the invention. Such variations are not to be regarded as a departure from the spirit and scope of the invention.

What is claimed is:

1. A medical device comprising:
    a collection wire configured for entering a patient's anatomy, the collection wire including a distal end with a fibrous structure comprising a plurality of tips, the plurality of tips being configured to attract stone fragments from the patient's anatomy, wherein the fibrous structure comprises a first end and an opposite second end, wherein a distalmost point of the distal end is between the first end and the second end, and wherein the plurality of tips include at least one of:
    i) a magnetic outer surface; and
    ii) a nanofunctional molecule bonded to an outer surface.

2. The medical device of claim 1 wherein the plurality of tips are a plurality of curled tips.

3. The medical device of claim 1 wherein the tips of the plurality of tips extend laterally from the distal end, the tips of the plurality of tips being spaced apart and positioned about the distal end in a spiral arrangement.

4. The medical device of claim 1 wherein each one of the plurality of tips comprises a filament.

5. The medical device of claim 4 wherein the filaments are intertwined into the fibrous structure.

6. The medical device of claim 5 wherein the filaments are coated with a flexible polymer or an adhesive.

7. The medical device of claim 1 further comprising a wire mesh that selectively surrounds the plurality of tips.

8. The medical device of claim 7 wherein the wire mesh selectively surrounds the plurality of tips by moving distally and proximally relative to the plurality of tips.

9. The medical device of claim 7 wherein the wire mesh is configured to collapse over the plurality of tips.

10. The medical device of claim 1 wherein the collection wire is formed of molded silicone.

11. The medical device of claim 1 wherein the collection wire is formed of molded plastic.

12. A method of collecting stone fragments from a patient's anatomy comprising:
    a) inserting a collection wire into the patient's anatomy, the collection wire including a distal end with a fibrous structure comprising a plurality of tips, the plurality of tips being configured to attract stone fragments from the patient's anatomy, wherein the fibrous structure comprises a first end and an opposite second end, wherein a distalmost point of the distal end is between the first end and the second end, and wherein the plurality of tips include at least one of:
    i) a magnetic outer surface; and
    ii) a nanofunctional molecule bonded to an outer surface;
    b) positioning a distal end of the collection wire near an anatomical region containing stone fragments, the distal end having a plurality of tips; and
    c) attracting the stone fragments to the collection wire with the plurality of tips.

13. The method of claim 12 further comprising surrounding the stone fragments and the plurality of tips with a wire mesh.

14. The method of claim 12 wherein the nanofunctional molecule bonded to the outer surface attracts the stone fragments.

15. The method of claim 12 further comprising a step of injecting an adhesive agent into the patient's anatomy prior to step c).

* * * * *